United States Patent
Srimohanarajah et al.

(10) Patent No.: US 11,712,307 B2
(45) Date of Patent: Aug. 1, 2023

(54) SYSTEM AND METHOD FOR MAPPING NAVIGATION SPACE TO PATIENT SPACE IN A MEDICAL PROCEDURE

(71) Applicant: SYNAPTIVE MEDICAL INC., Toronto (CA)

(72) Inventors: Kirusha Srimohanarajah, Toronto (CA); Dorothy Lui, Toronto (CA); Gal Sela, Toronto (CA)

(73) Assignee: Synaptive Medical Inc.

( * ) Notice: Subject to any disclaimer, the term of this patent is extended or adjusted under 35 U.S.C. 154(b) by 95 days.

(21) Appl. No.: 17/302,709

(22) Filed: May 11, 2021

(65) Prior Publication Data

US 2021/0259785 A1 Aug. 26, 2021

Related U.S. Application Data

(63) Continuation of application No. 15/506,627, filed as application No. PCT/CA2015/050573 on Jun. 22, 2015, now Pat. No. 11,045,257.

(51) Int. Cl.
| | |
|---|---|
| A61B 34/20 | (2016.01) |
| A61B 90/00 | (2016.01) |
| A61B 5/00 | (2006.01) |
| A61B 5/06 | (2006.01) |
| A61B 34/10 | (2016.01) |
| A61B 90/50 | (2016.01) |

(52) U.S. Cl.
CPC ............... *A61B 34/20* (2016.02); *A61B 5/00* (2013.01); *A61B 5/06* (2013.01); *A61B 5/064* (2013.01); *A61B 34/10* (2016.02); *A61B 90/39* (2016.02); *A61B 2034/107* (2016.02); *A61B 2034/2055* (2016.02); *A61B 2090/364* (2016.02); *A61B 2090/3983* (2016.02); *A61B 2090/502* (2016.02)

(58) Field of Classification Search
CPC .. A61B 34/20; A61B 5/00; A61B 5/06; A61B 5/064; A61B 34/10; A61B 90/39; A61B 2034/107; A61B 2034/2055; A61B 2090/364; A61B 2090/3983; A61B 2090/502; A61B 2090/3995; A61B 5/062
See application file for complete search history.

(56) References Cited

U.S. PATENT DOCUMENTS

| | | | | |
|---|---|---|---|---|
| 5,871,445 | A * | 2/1999 | Bucholz | A61B 5/0064 600/407 |
| 2002/0082498 | A1 * | 6/2002 | Wendt | G16H 40/67 348/E13.059 |
| 2002/0183608 | A1 * | 12/2002 | Marmulla | A61B 90/39 600/407 |
| 2010/0172567 | A1 * | 7/2010 | Prokoski | G06K 9/00 348/47 |

\* cited by examiner

*Primary Examiner* — Yi-Shan Yang
*Assistant Examiner* — Alexei Bykhovski

(57) ABSTRACT

An apparatus is provided that is visible by both a three dimensional (3D) scanner system of a medical navigation system and a camera of the medical navigation system. The apparatus involves a rigid member and a plurality of markers attached to the rigid member. Each of the plurality of markers includes a reflective surface portion visible by the camera and a distinct identifiable portion visible by the 3D scanner system. The apparatus further involves a connector mechanism to connect the apparatus to a reference location. The apparatus is in a field of view of the 3D scanner system and the camera within a timeframe of the 3D scan.

20 Claims, 12 Drawing Sheets

SYSTEM AND METHOD FOR MAPPING NAVIGATION SPACE TO PATIENT SPACE IN A MEDICAL PROCEDURE

CROSS-REFERENCE TO RELATED APPLICATION(S)

This document is a continuation application which claims the benefit of, and priority to: U.S. patent application Ser. No. 15/506,627, filed on Feb. 24, 2017, entitled "SYSTEM AND METHOD FOR MAPPING NAVIGATION SPACE TO PATIENT SPACE IN A MEDICAL PROCEDURE" and International Patent Application No. PCT/CA2015/050573, filed on Jun. 22, 2015, entitled "SYSTEM AND METHOD FOR MAPPING NAVIGATION SPACE TO PATIENT SPACE IN A MEDICAL PROCEDURE," which are incorporated herein by reference in their entirety.

TECHNICAL FIELD

The present disclosure generally relates to neurosurgical or medical procedures and more specifically relates to a system and method for mapping navigation space to patient space in a medical procedure.

BACKGROUND

In the field of medicine, imaging and image guidance are significant components of clinical care. From diagnosis and monitoring of disease to planning of the surgical approach, guidance during procedures, and follow-up after the procedure is complete, imaging and image guidance provides effective and multifaceted treatment approaches, for a variety of procedures, including surgery and radiation therapy. Targeted stem cell delivery, adaptive chemotherapy regimes, and radiation therapy are only a few examples of procedures utilizing imaging guidance in the medical field.

Advanced imaging modalities, such as magnetic resonance imaging (MRI), have led to improved rates and accuracy of detection, diagnosis, and staging in several fields of medicine, including neurology, wherein imaging of diseases, such as brain cancer, stroke, intra-cerebral hemorrhage (ICH), and neurodegenerative diseases, such as Parkinson's and Alzheimer's, are performed. As an imaging modality, MRI enables three-dimensional visualization of tissue with high contrast in soft tissue without the use of ionizing radiation. This modality is often used in conjunction with other modalities such as ultrasound (US), positron emission tomography (PET) and computed X-ray tomography (CT), by examining the same tissue using the different physical principals available with each modality. CT is often used to visualize boney structures and blood vessels when used in conjunction with an intra-venous agent such as an iodinated contrast agent. MRI may also be performed using a similar contrast agent, such as an intra-venous gadolinium based contrast agent which has pharmaco-kinetic properties that enable visualization of tumors and break-down of the blood brain barrier. These multi-modality solutions can provide varying degrees of contrast between different tissue types, tissue function, and disease states. Imaging modalities can be used in isolation, or in combination, to better differentiate and diagnose disease.

In neurosurgery, for example, brain tumors are typically excised through an open craniotomy approach guided by imaging. The data collected in these solutions typically consists of CT scans with an associated contrast agent, such as iodinated contrast agent, as well as MRI scans with an associated contrast agent, such as gadolinium contrast agent. Also, optical imaging is often used in the form of a microscope to differentiate the boundaries of the tumor from healthy tissue, known as the peripheral zone. Tracking of instruments relative to the patient and the associated imaging data is also often achieved by way of external hardware systems such as mechanical arms, or radiofrequency or optical tracking devices. As a set, these devices are commonly referred to as surgical navigation systems.

Three dimensional (3D) sensor systems are increasingly being used in a wide array of applications, including medical procedures. These sensor systems determine the shape and/or features of an object positioned in a scene of the sensor system's view. In recent years, many methods have been proposed for implementing 3D modeling systems that are capable of acquiring fast and accurate high resolution 3D images of objects for various applications.

Triangulation-based 3D sensor systems and methods typically involve one or more projectors as a light source for projecting onto a surface and one or more cameras at a defined, typically rectified relative position from the projector for imaging the lighted surface. The camera and the projector, therefore, have different optical paths; and the distance between them is referred to as the baseline. Through knowledge of the baseline distance as well as projection and imaging angles, known geometric/triangulation equations are utilized to determine distance to the imaged object. The main differences among the various triangulation methods in the related art lie in the method of projection as well as the type of light projected, typically structured light, and in the process of image decoding to obtain three dimensional data.

A 3D sensor system may be contemplated as a novel extension of a surgical navigation systems. One popular triangulation based 3D sensor system is created by Mantis Vision®, which utilizes a single frame structured light active triangulation system to project infrared light patterns onto an environment. To capture 3D information, a projector overlays an infrared light pattern onto the scanning target. Then a digital camera and a depth sensor, synched with the projector, captures the scene with the light reflected by the object for at least the timeframe of one frame of the 3D scan. The technology works even in complete darkness, since it includes its own illumination; and, in bright environments the quality of the resulting image depends on the hardware used.

During a medical procedure, navigation systems require a registration to transform between the physical position of the patient in the operating room and the volumetric image set, e.g., MRI/CT, being navigated to. Conventionally, this registration is done to the position of a reference tool, which is visible by the tracking system and stays fixed in position and orientation relative to the patient throughout the procedure.

This registration is typically accomplished through correspondence touch points, e.g., either fiducial or anatomic points. Such an approach to registration has a number of disadvantages, including requiring fiducials to be placed before scans, requiring points to be identified, providing for a limited number of points, touch point collection is subject to user variability, and the physical stylus used for collecting the points can deform or deflect patient skin position. Another conventional approach to collecting the touch points includes performing a surface tracing of the patient drawn as a line which is matched to the image set surface contour using either a stylus pointer or a laser pointer. Such an approach to registration has a number of disadvantages, including providing for a limited number of points, and the physical stylus can deform or deflect patient skin position. Yet another conventional approach to collecting the touch points includes using a mask which requires a high level of operator training and is operator dependent. This approach also provides only a limited number of points.

Other common limitations of the conventional approaches to registration discussed above include a stylus that needs to remain visible to the tracking system, which not necessarily possible depending on a patient's surgical position or may introduce surgical restrictions that need to be accounted in planning, and error accumulation where touch point or tracing collection is of low quality resulting in error propagation through subsequent steps of the registration. Further, using the conventional methods, if registration is lost, re-registration is difficult if not possible to be completed again during surgery.

Therefore, a need exists for an improved system and method for mapping navigation space to patient space in a medical procedure.

SUMMARY

One aspect of the present disclosure provides an apparatus that is visible by both a three dimensional (3D) scanner system of a medical navigation system and a camera of the medical navigation system. The apparatus comprises a rigid member and a plurality of markers attached to the rigid member. Each of the plurality of markers includes a reflective surface portion visible by the camera and a distinct identifiable portion visible by the 3D scanner system. The apparatus further comprises a connector mechanism to connect the apparatus to a reference location. The apparatus is in a field of view of the 3D scanner system and the camera within a timeframe of the 3D scan.

Another aspect of the present disclosure provides a method of registering a patient for a medical procedure with a medical navigation system using an apparatus visible by both a three dimensional (3D) scanner system of the medical navigation system and a camera of the medical navigation system. The method comprises generating and receiving 3D scan data from the 3D scanner representative of a 3D scan of at least a portion of the patient, the 3D scan including distinct identifiable portions of the apparatus visible by the 3D scanner system; generating and receiving image data from the camera, the image data including reflective surface portions of the apparatus visible by the camera; loading saved medical image data, the saved medical data including preoperative image data saved during a previous scan of at least a portion of the patient; and performing a transformation mapping to create a single unified virtual coordinate space based on the 3D scan data, the image data, and the medical image data.

A further understanding of the functional and advantageous aspects of the disclosure is realized by reference to the following detailed description and drawings.

BRIEF DESCRIPTION OF THE DRAWINGS

Embodiments are described, by way of example only, with reference to the drawings, in which.

DETAILED DESCRIPTION

Figure 1:
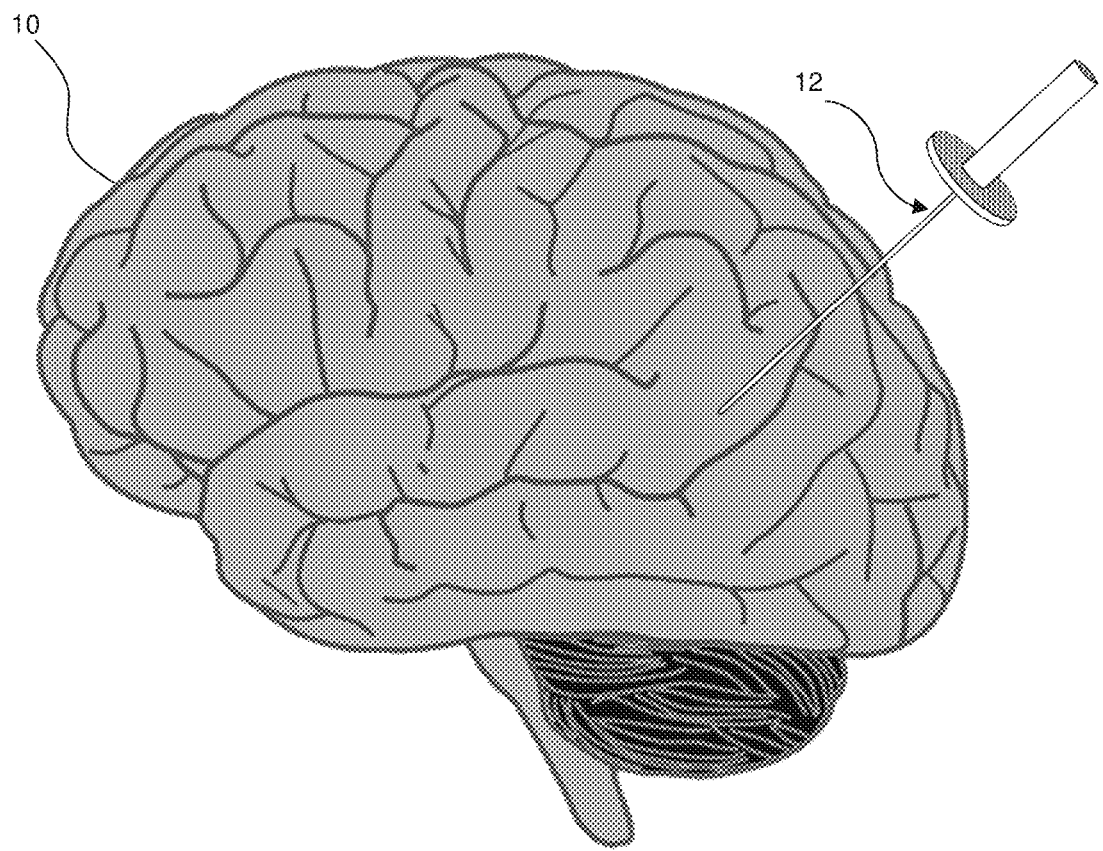
FIG. 1 is a diagram illustrating the insertion of an access port into a human brain, for providing access to internal brain tissue during a medical procedure.

Various embodiments and aspects of the disclosure are described with reference to below details discussed. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about," "approximately," and "substantially" are meant to cover variations that may exist in the upper and lower limits of the ranges of values, such as variations in properties, parameters, and dimensions. In one non-limiting example, the terms "about," "approximately," and "substantially" mean plus or minus 10 percent or less.

Unless defined otherwise, all technical and scientific terms used herein are intended to have the same meaning as commonly understood by one of ordinary skill in the art. Unless otherwise indicated, such as through context, as used herein, the following terms are intended to have the following meanings:

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

Embodiments of the present disclosure provide imaging devices that are insertable into a subject or patient for imaging internal tissues, and methods of use thereof. Some embodiments of the present disclosure relate to minimally invasive medical procedures that are performed via an access port, whereby surgery, diagnostic imaging, therapy, or other medical procedures, e.g. minimally invasive medical procedures, are performed based on access to internal tissue through the access port.

The present disclosure is generally related to medical procedures and specifically related to neurosurgery and minimally invasive port-based surgery.

In the example of a port-based surgery, a surgeon or robotic surgical system may perform a surgical procedure involving tumor resection in which the residual tumor remaining after is minimized, while also minimizing the trauma to the healthy white and grey matter of the brain. In such procedures, trauma may occur, for example, due to contact with the access port, stress to the brain matter, unintentional impact with surgical devices, and/or accidental resection of healthy tissue. A key to minimizing trauma is ensuring that the spatial location of the patient as understood by the surgeon and the surgical system is as accurate as possible.

Referring to FIG. 1, this diagram illustrates the insertion of an access port 12 into a human brain 10, for providing access to internal brain tissue during a medical procedure, in accordance with an embodiment of the present disclosure. The access port 12 is inserted into a human brain 10, providing access to internal brain tissue. The access port 12 may include instruments, such as catheters, surgical probes, or cylindrical ports, such as the NICO® BrainPath®. Surgical tools and instruments may then be inserted within the lumen of the access port 12 in order to perform surgical, diagnostic or therapeutic procedures, such as resecting tumors as necessary. The present disclosure applies equally well to catheters, DBS needles, and a biopsy procedure, as well as to biopsies and/or catheters in other medical procedures performed on other parts of the body where head immobilization is needed.

Still referring to FIG. 1, in the example of a port-based surgery, a straight or linear access port 12 is typically guided down a sulci path of the brain 10. Surgical instruments would then be inserted down the access port 12. Optical tracking systems (not shown), which may be used in the medical procedure, track the position of a part of the instrument that is within line-of-site of the optical tracking camera. These optical tracking systems also require a reference to the patient to know where the instrument is relative to the target, e.g., a tumor, of the medical procedure. These optical tracking systems require a knowledge of the dimensions of the instrument being tracked so that, for example, the optical tracking system knows the position in space of a tip of a medical instrument relative to the tracking markers being tracked.

Figure 2:
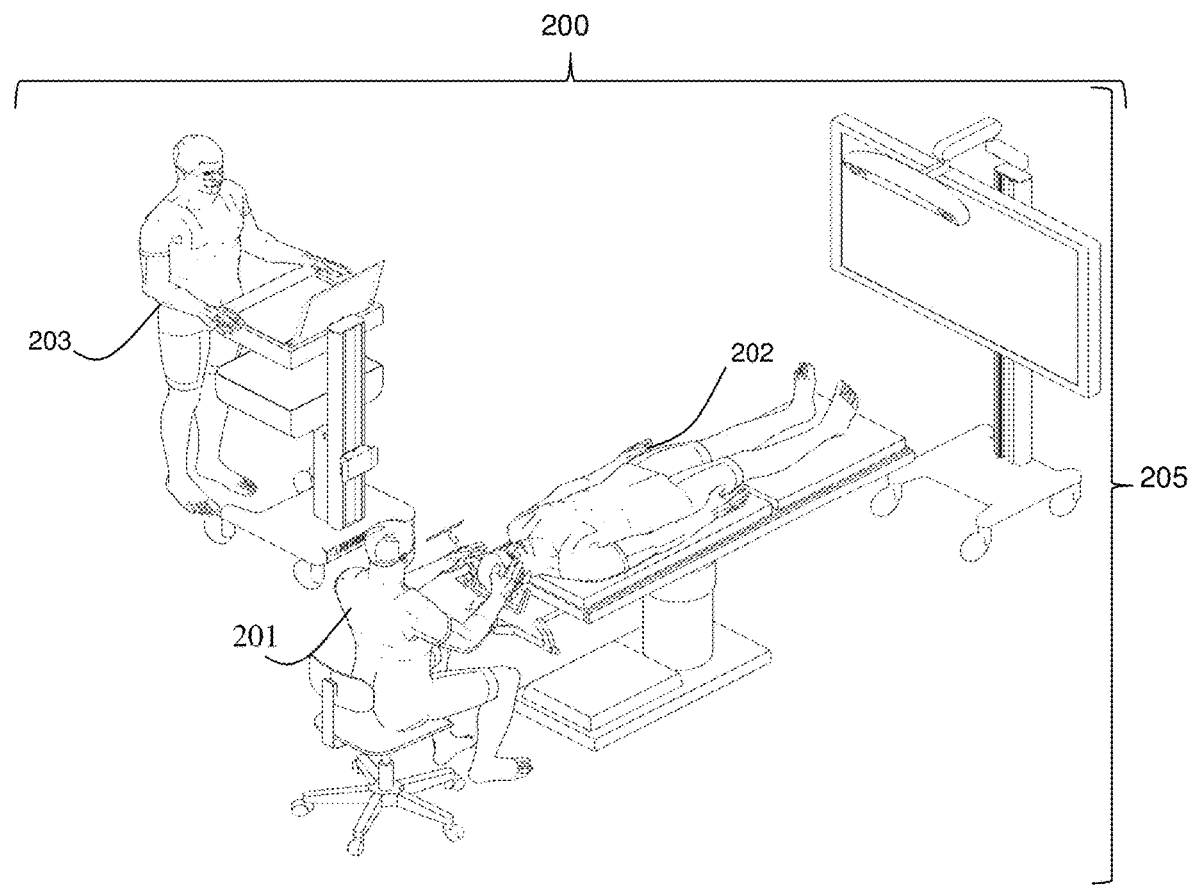
FIG. 2 is a diagram illustrating an exemplary medical navigation system in a medical environment to support minimally invasive access port-based surgery.

Referring to FIG. 2, this diagram illustrates an exemplary medical navigation system 205 in a medical environment 200 which may be used to support navigated image-guided surgery, in accordance with an embodiment of the present disclosure. A surgeon 201 conducts a surgery on a patient 202 in an operating room (OR) environment. A medical navigation system 205 comprising an equipment tower, tracking system, displays and tracked instruments assist the surgeon 201 during his procedure. An operator 203 is also present to operate, control, and provide assistance for the medical navigation system 205.

Figure 3:
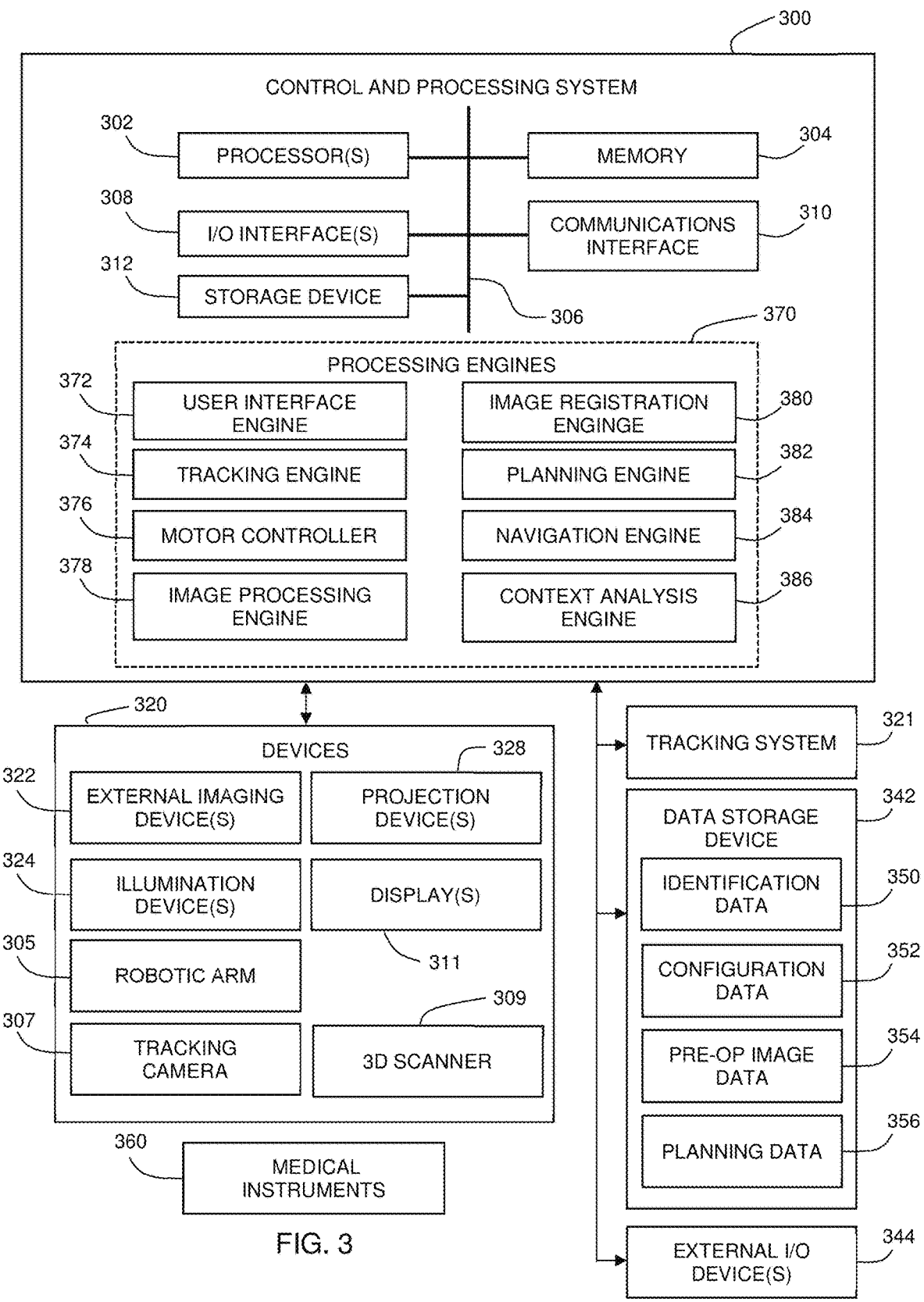
FIG. 3 is a block diagram illustrating a control and processing system usable in the navigation system, as shown in FIG. 2.

Referring to FIG. 3, this block diagram illustrates a control and processing system 300 usable in the medical navigation system 205, as shown in FIG. 2, e.g., as part of the equipment tower, in accordance with an embodiment of the present disclosure. In one example, the control and processing system 300 comprises one or more processors 302, a memory 304, a system bus 306, one or more input/output (I/O) interfaces 308, a communications interface 310, and storage device 312. Control and processing system 300 may be interfaced with other external devices, such as a tracking system 321, a data storage device 342, and external user input/output (I/O) devices 344, which may include, for example, one or more of a display, keyboard, mouse, sensors attached to medical equipment, foot pedal, and microphone and speaker (not shown). Data storage device 342 may be any suitable data storage device, such as a local or remote computing device, e.g., a computer, hard drive, digital media device, or server, having a database stored thereon. The data storage device 342 includes identification data 350 for identifying one or more medical instruments 360 and configuration data 352 that associates customized configuration parameters with one or more medical instruments 360. Data storage device 342 may also include preoperative (pre-op) image data 354 and/or planning data 356, e.g. medical procedure planning data. Although data storage device 342 is shown as a single device, understood is that, in other embodiments, the data storage device 342 comprises multiple storage devices.

Still referring to FIG. 3, the medical instruments 360 are identifiable by the control and processing system 300. The medical instruments 360 are coupled with, and controlled by, the control and processing system 300. Alternatively, the medical instruments 360 are operated, or otherwise employed, independent of the control and processing system 300. Tracking system 321 may be employed to track one or more of medical instruments 360 and spatially register the one or more tracked medical instruments 360 to an intraoperative reference frame. For example, the medical instruments 360 may include tracking markers, such as tracking spheres, that may be recognizable by a tracking camera 307. In one example, the tracking camera 307 comprises an infrared (IR) tracking camera. In another example, as sheath, placed over a medical instrument 360, is coupled with, and controlled by, the control and processing system 300.

Still referring to FIG. 3, the control and processing system 300 also interfaces with a number of configurable devices and intraoperatively reconfigures one or more of such devices based on configuration parameters obtained from configuration data 352. Examples of devices 320 include one or more external imaging devices 322, one or more illumination devices 324, a robotic arm 305, one or more projection devices 328, a 3D scanner 309, and one or more displays 311.

Still referring to FIG. 3, exemplary aspects of embodiments in the present disclosure can be implemented via the processor(s) 302 and/or the memory 304. For example, the functionalities, herein described, are partially implemented via hardware logic in the processor 302, and partially implemented using the instructions stored in the memory 304, as one or more processing engines 370, e.g., processing modules. Example processing engines 370 include, but are not limited to, a user interface engine 372, a tracking engine 374, a motor controller 376, an image processing engine 378, image registration engine 380, procedure planning engine 382, navigation engine 384, and a context analysis module 386. While the example processing engines or modules are shown separately, in one example, the processing engines 370 are stored in the memory 304; and the processing modules are collectively referred as processing engines 370. Understood is that the system 300 is not intended to be limited to the components shown. One or more components of the control and processing system 300 are provided as an external component or device. In one example, the navigation engine 384 is provided as an external navigation system that is integrated with the control and processing system 300. Some embodiments are implemented using processor the 302 without additional instructions stored in the memory 304. Some embodiments are implemented using the instructions stored in the memory 304 for execution by one or more general purpose microprocessors. Thus, the present disclosure is not limited to a specific configuration of hardware and/or software. While some embodiments are implemented in fully functioning computers and computer systems, various embodiments are capable of being distributed as a computing product in a variety of forms and are capable of being applied, regardless of the particular type of machine or computer-readable media used to actually effect the distribution.

Still referring to FIG. 3 and referring back to FIG. 2, according to one aspect of the present disclosure, one purpose of the navigation system 205, which may include the control and processing unit 300, is to provide tools to the neurosurgeon that will lead to the most informed, least damaging neurosurgical operations. In addition to removal of brain tumors and intracranial hemorrhages (ICH), the navigation system 205 is appliable to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, aspects of the present disclosure may be applied to any suitable medical procedure. While one example of a navigation system 205 is provided that may be used with aspects of the present disclosure, any suitable navigation system may be used, such as a navigation system using optical tracking instead of infrared cameras.

Figure 4A:
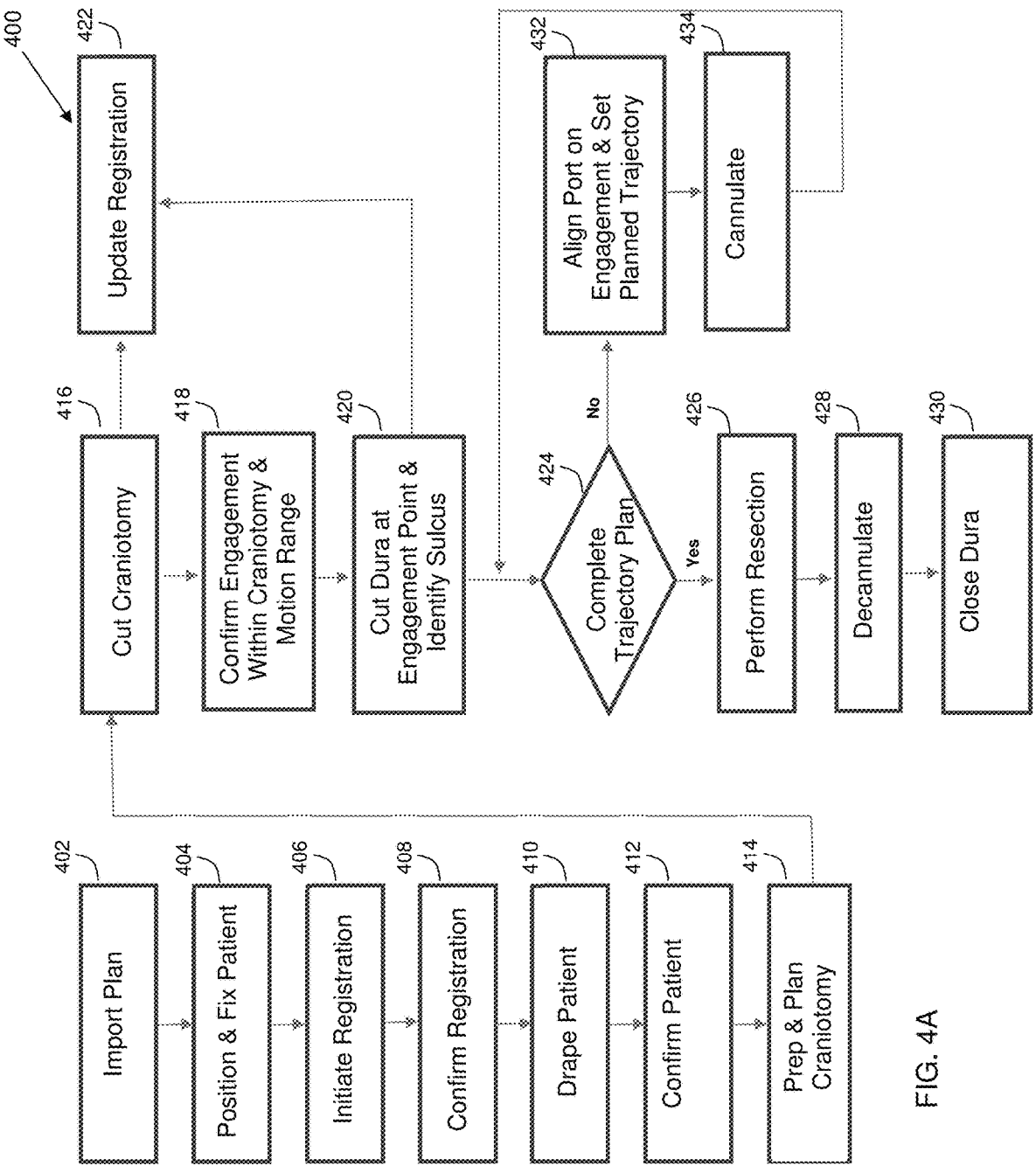
FIG. 4A is a flow chart illustrating a method of performing a port-based surgical procedure using a navigation system, as shown in FIG. 2.

Referring to FIG. 4A, this flow chart illustrates a method 400 of performing a port-based surgical procedure using a navigation system, such as the medical navigation system 205, as shown in FIG. 2, in accordance with an embodiment of the present disclosure. At a first block 402, the port-based surgical plan is imported. A detailed description of the process to create and select a surgical plan is outlined in international publication WO/2014/139024, entitled "PLANNING, NAVIGATION AND SIMULATION SYSTEMS AND METHODS FOR MINIMALLY INVASIVE THERAPY", which claims priority to U.S. Provisional Patent Application Ser. Nos. 61/800,155 and 61/924,993, which are all hereby incorporated by reference in their entirety. Once the plan has been imported into the navigation system at the block 402, the patient is placed on a surgical bed. The head position is confirmed with the patient plan in the navigation system (block 404), which, in one example, may be implemented by a computer or controller forming part of the equipment tower.

Still referring to FIG. 4A, next, registration of the patient is initiated (block 406). The phrase "registration" or "image registration" refers to the process of transforming different sets of data into one coordinate system. Data may include multiple photographs, data from different sensors, times, depths, or viewpoints. The process of "registration" is used in the present disclosure for medical imaging in which images from different imaging modalities are co-registered. Registration is used in order to be able to compare or integrate the data obtained from these different modalities to the patient in physical space.

Still referring to FIG. 4A, appreciated is that numerous registration techniques are available and one or more of the techniques may be applied to the present example. Non-limiting examples include intensity-based methods that compare intensity patterns in images via correlation metrics, while feature-based methods find correspondence between image features such as points, lines, and contours. Image registration methods may also be classified according to the transformation models that they use to relate the target image space to the reference image space. Another classification can be made between single-modality and multi-modality methods. Single-modality methods typically register images in the same modality acquired by the same scanner or sensor type, for example, a series of magnetic resonance (MR) images may be co-registered, while multi-modality registration methods are used to register images acquired by different scanner or sensor types, for example, in magnetic resonance imaging (MRI) and positron emission tomography (PET). In the present disclosure, multi-modality registration methods may be used in medical imaging of the head and/or the brain as images of a subject are frequently obtained from different scanners. Examples include registration of brain computerized tomography CT/MRI images or PET/CT images for tumor localization, registration of contrast-enhanced CT images against non-contrast-enhanced CT images, and registration of ultrasound and CT to patient in physical space.

Figure 4B:
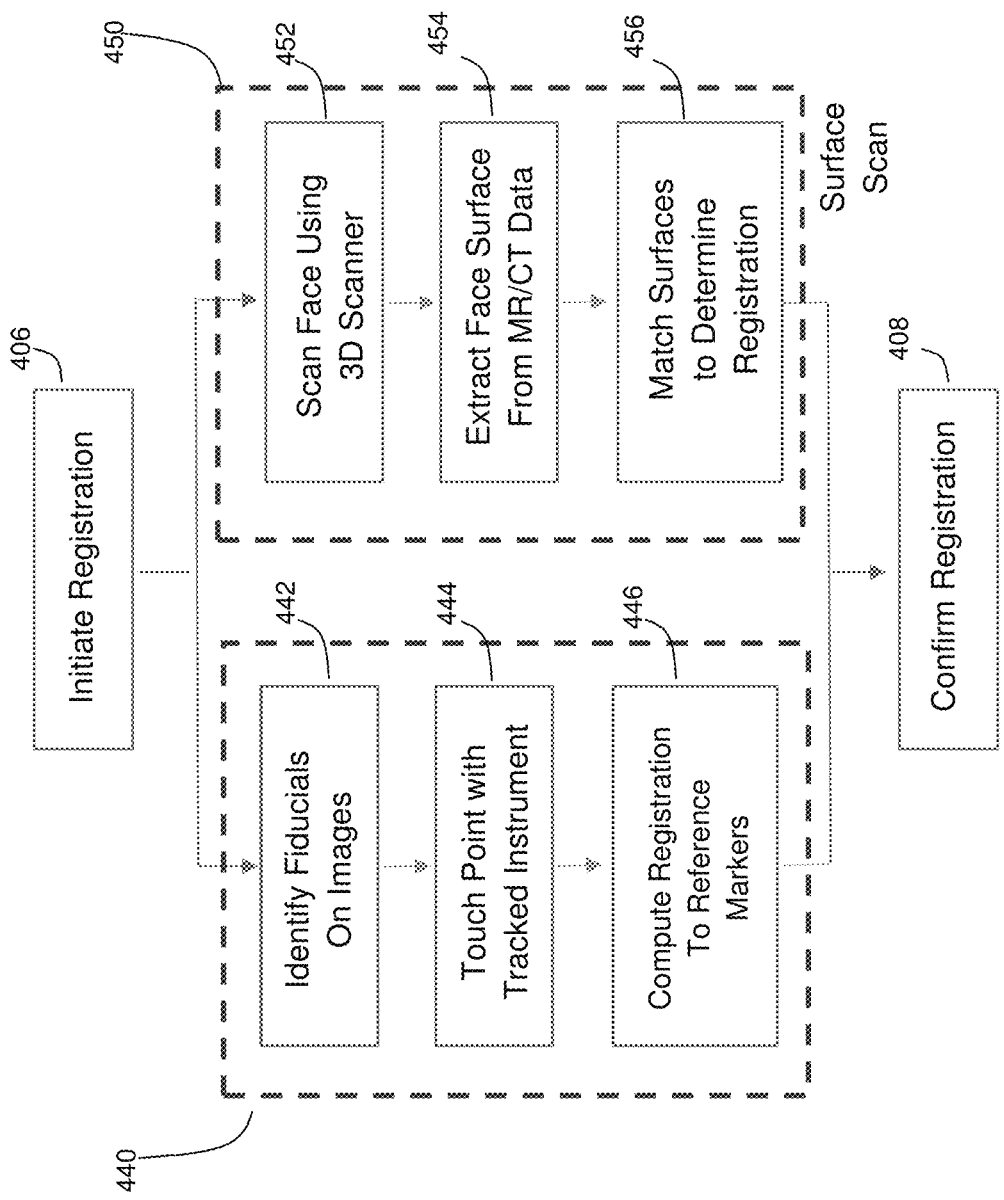
FIG. 4B is a flow chart illustrating a method of registering a patient for a surgical procedure, as shown in FIG. 4A in greater detail.

Referring now to FIG. 4B, this flow chart illustrates a method of registering a patient for a surgical procedure, as directed by block 406 shown in FIG. 4A, in greater detail, in accordance with an embodiment of the present disclosure. If the use of fiducial touch points (block 440) is contemplated, the method involves first identifying fiducials on images (block 442), then touching the touch points with a tracked instrument (block 444). Next, the navigation system 205 computes the registration to reference markers (block 446).

Referring now to FIG. 4B, alternatively, registration can also be completed by conducting a surface scan procedure (block 450), which may be applied to aspects of the present disclosure. The block 450 is presented to show an alternative approach. First, the face is scanned using a 3D scanner (block 452). Next, the face surface is extracted from MR/CT data (block 454). Finally, surfaces are matched to determine registration data points (block 456).

Referring back to FIGS. 4A and 2, upon completion of either the fiducial touch points (440) or surface scan (450) procedures, the data extracted is computed and used to confirm registration at block 408. Once registration is confirmed (block 408), the patient 202 is draped (block 410). Typically, draping involves covering the patient 202 and surrounding areas with a sterile barrier to create and maintain a sterile field during the surgical procedure. The purpose of draping is to eliminate the passage of microorganisms, e.g., bacteria, between non-sterile and sterile areas. At this point, conventional navigation systems require that the non-sterile patient reference is replaced with a sterile patient reference of identical geometry location and orientation. Numerous mechanical methods may be used to minimize the displacement of the new sterile patient reference relative to the non-sterile one that was used for registration, but that some error will exist is inevitable. This error directly translates into registration error between the surgical field and the pre-surgical images. In fact, the farther away points of interest are from the patient reference, the worse the error will be.

Referring back to FIGS. 4A, 1 and 2, upon completion of draping (block 410), the patient engagement points are confirmed (block 412) and then the craniotomy is prepared and planned (block 414). Upon completion of the preparation and planning of the craniotomy (block 414), the craniotomy is cut and a bone flap is temporarily removed from the skull to access the brain 10 (block 416). Registration data is updated with the navigation system 205 at this point (block 422). Next, the engagement within craniotomy and the motion range are confirmed (block 418). Next, the procedure advances to cutting the dura at the engagement points and identifying the sulcus (block 420).

Still referring back to FIGS. 4A, 1 and 2, thereafter, the cannulation process is initiated (block 424). Cannulation involves inserting a port into the brain, typically along a sulci path as identified at 420, along a trajectory plan. Cannulation is typically an iterative process that involves repeating the steps of aligning the port on engagement and setting the planned trajectory (block 432) and then cannulating to the target depth (block 434) until the complete trajectory plan is executed (block 424).

Still referring back to FIGS. 4A, 1 and 2, once cannulation is complete, the surgeon 201 then performs resection (block 426) to remove part of the brain 10 and/or tumor of interest. The surgeon 201 then decannulates (block 428) by removing the port 12 and any tracking instruments from the brain 10. Finally, the surgeon 201 closes the dura and completes the craniotomy (block 430). Some aspects shown are specific to port-based surgery, such as portions of blocks 428, 420, and 434, but the appropriate portions of these blocks may be skipped or suitably modified when performing non-port based surgery.

Figure 5:
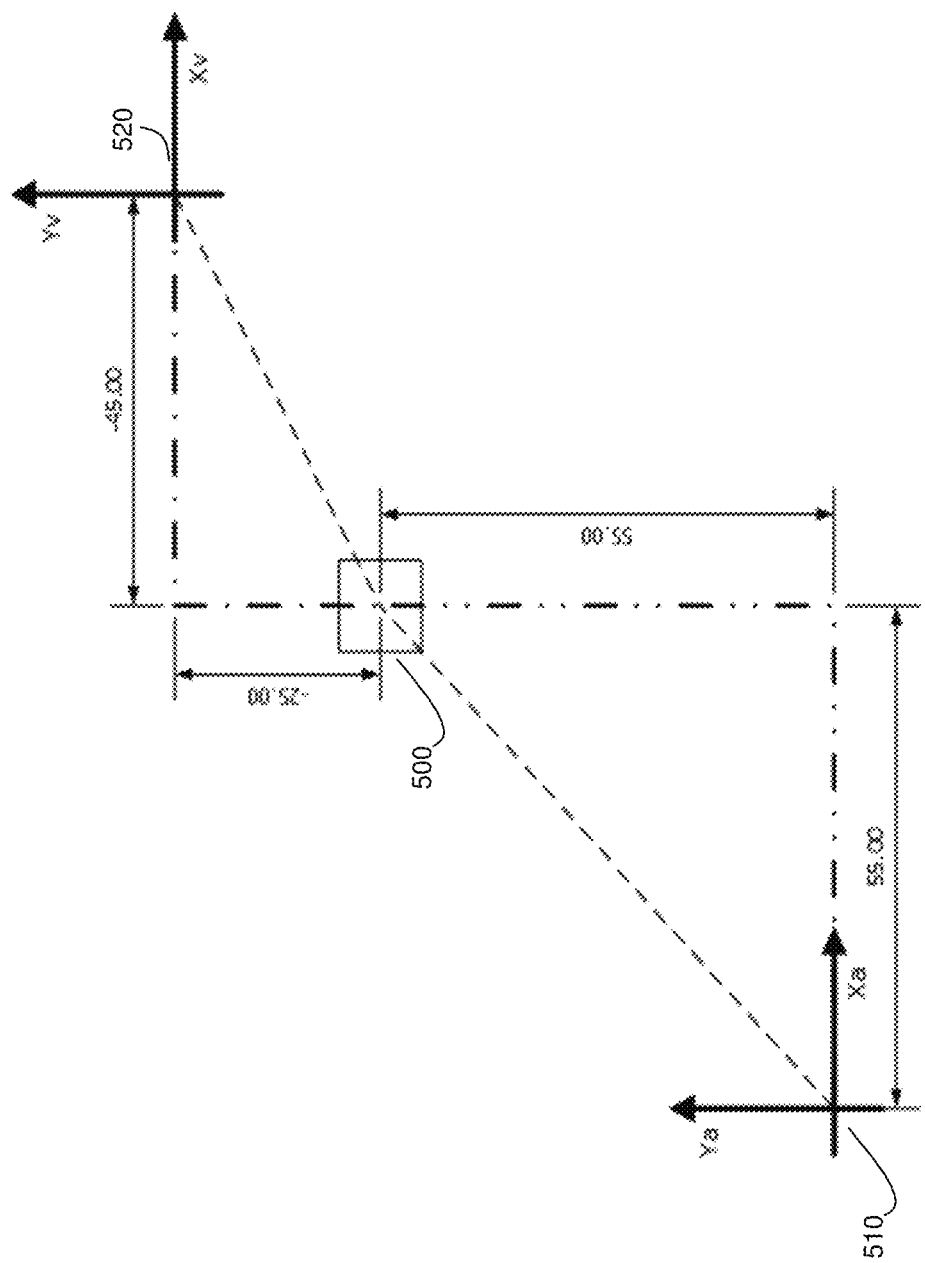
FIG. 5 is a flow chart illustrating the use of multiple patient reference markers for registration.

Referring to FIG. 5, this flow chart illustrates the use of multiple patient reference markers 604 (FIG. 6) for registration, in accordance with an embodiment of the present disclosure. A registration process, similar to that which may be used in block 456, as shown in FIG. 4B, is shown for creating a common coordinate space comprising amalgamated virtual and actual coordinate spaces. The common coordinate space comprises both an actual coordinate space and a virtual coordinate space, where the actual coordinate space contains actual objects that exist in space and the virtual coordinate space contains virtual objects that are generated in a virtual space. The common coordinate space containing both the aforementioned actual and virtual objects may be produced as follows:

Still referring to FIG. 5, in order to form a common coordinate space composed of the amalgamated virtual and actual coordinate spaces, the two spaces are coupled with a "common reference coordinate," having a defined position that can be located in both the actual and virtual coordinate spaces. An example of such a common reference coordinate 500 and actual and virtual coordinate space origins 510, 520, are provided. Once the common reference coordinate position is acquired in both spaces, the common reference coordinate position can be used to correlate the position of any point in one coordinate space to the other. The correlation is determined by equating the locations of the common reference coordinate in both spaces and solving for an unknown translation variable for each degree of freedom defined in the two coordinate spaces.

Still referring to FIG. 5, these translation variables may then be used to transform a coordinate element of a position in one space to an equivalent coordinate element of a position in the other. An example correlation can be derived from the diagram depicting a two dimensional coordinate space. The common reference coordinates 500 position is determined relative to the actual coordinate space origin 510 and the virtual coordinate space origin 520. The common reference coordinates positions can be derived from the diagram as follows: $(X_{cra}, Y_{cra})=(55, 55)$ and $(X_{crv}, Y_{crv})=(-25, -45)$, wherein the subscript "cra" denotes the common reference coordinate position relative to the actual coordinate space origin, and wherein the subscript "crv" denotes the common reference coordinate position relative to the virtual coordinate space origin. Utilizing a generic translation equation describing any points $(Y_a, X_a)$ and $(Y_v, X_v)$, wherein the subscript "a" denotes the coordinates of a point relative to the actual coordinate space origin 510, and the subscript "v" denotes the coordinate of a point relative to the virtual coordinate space origin 520, the individual coordinates are equated from each space to solve for translation variables $(Y_T, X_T)$, wherein the subscript "T" denotes the translation variable as follows: $Y_a=Y_v+Y_T$ and $X_a=X_v+X_T$.

Still referring to FIG. 5, now substituting the derived values of our points, the translation variable is solved as follows: $55=-45+Y_T$, $100=Y_T$, and $55=-25+X_T$, $80=X_T$. Utilizing this translation variable, any point, i.e. $(Y_v, X_v)$ in the virtual coordinate space may be transformed into an equivalent point in the actual coordinate space through the below two generic transformation equations. Noted is that these equations can be rearranged to transform any coordinate element of a position from the actual coordinate space into an equivalent coordinate element of a position in the virtual coordinate space as well as follows: $Y_a=Y_v+100$ and $X_a=X_v+80$. Therefore, this transformation allows the respective positions of the virtual objects and the actual objects to be simultaneously defined in both the actual coordinate space and the virtual coordinate space. Once the correlation is determined, the actual coordinate space and the virtual coordinate space become coupled and result in the formation of a common coordinate space that may be used to register virtual objects and actual objects. Noted is that these virtual objects and actual objects can simultaneously be superimposed in the common coordinate space, e.g., they can occupy the same coordinates.

Still referring to FIG. 5 and referring back to FIG. 3, in an embodiment of the present disclosure, using a handheld three dimensional (3D) surface scanner system, such as the 3D scanner 309, a full array or nearly full array scan of a patient's surface can be achieved, as opposed to 1D line or a 2D grid of point depths with the conventional approaches. This scan may provide an order of magnitude greater point information than the surface tracing methods used in conventional approaches. Using a dense point cloud provided by the 3D scanner 309, this point cloud may be mapped to the extracted surface of the MR/CT volumetric scan data, e.g., the pre-op image data 354, to register the patient's physical position to the volumetric data. The tracking system 321, e.g., part of the navigation system 205, has no reference to the point cloud data. Therefore, a tool may be provided that is visible to both the tracking system 321 and the 3D scanner 309. A transformation between the tracking system's camera space and the 3D scanner space may be identified so that the point cloud, provided by the 3D scanner 309 and the tracking system 321, can be registered to the patient space. A transformation similar to, or based on, the transformation, as described in connection with FIG. 5, may be used.

Still referring to FIG. 5 and referring back to FIG. 3, in an embodiment of the present disclosure, provided is a tracking tool (not shown) that is at least partially optimized for visibility and tracking by both the tracking system 321 and a 3D scanner system, such as the 3D scanner 309. In one example, the 3D scanner 309 comprises a colour 3D scanner. The 3D scanner 309 is used to collect a colour point cloud which is defined in the patient space. To determine a transformation mapping between the tracking system 321 and the patient space, the tracking tool is identifiable in both spaces. While guidelines for tool configuration compatibility with the tracking system 321 may exist, no such rules exist for creating targets for extraction within point clouds. In one example, a cross-compatible tool (not shown) may be configured using three retro-reflective circular targets placed at unique distances from one another on a single rigid plane. Each target may include an IR retro-reflective center for visibility by the tracking system 321 and is surrounded by a high contrast coloured ring which enables straight forward extraction from the output point cloud collected from the 3D scanner 309.

Figure 6:
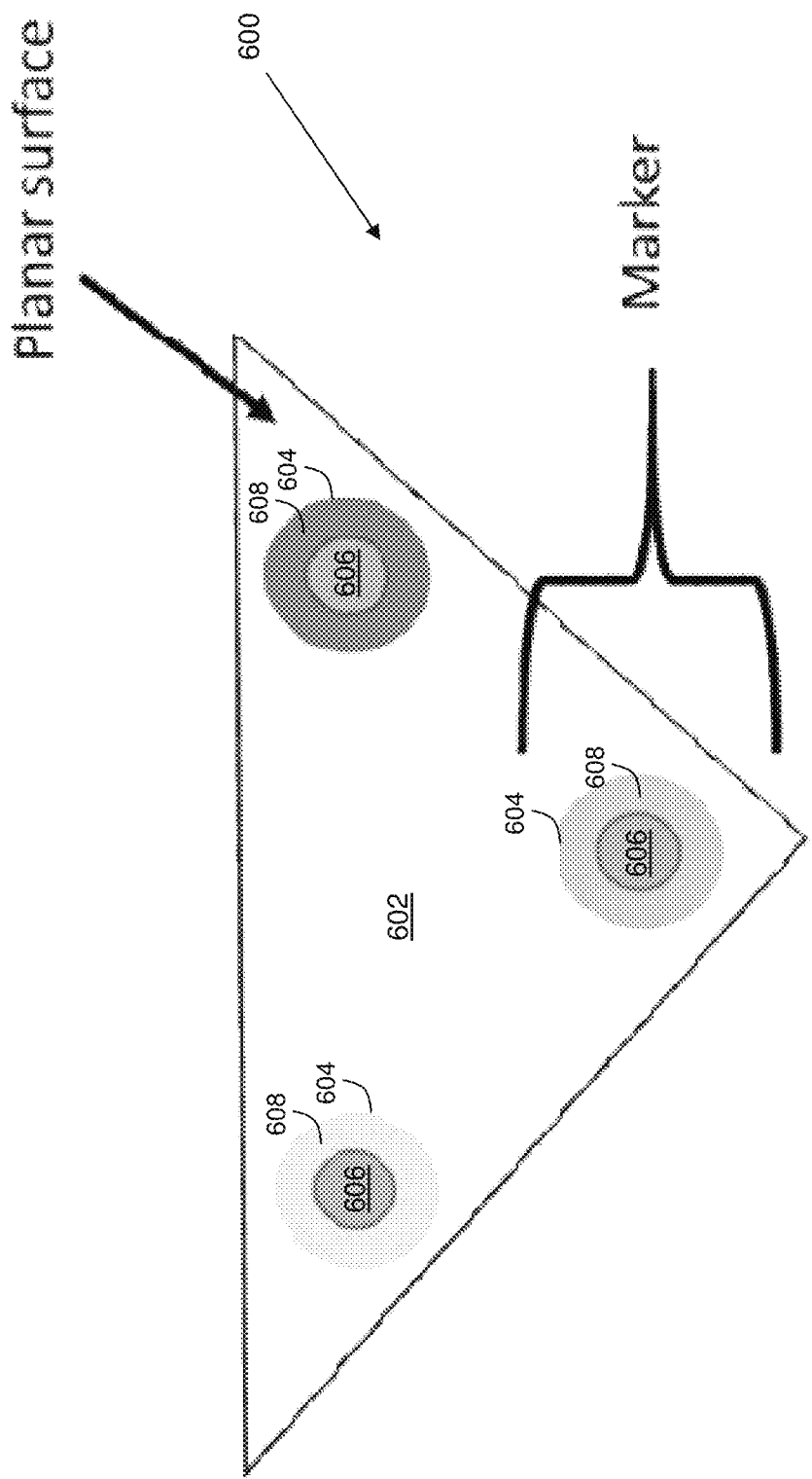
FIG. 6 is a diagram illustrating a wearable apparatus usable with the medical navigation system and the control and processing system, as respectively shown in FIGS. 2 and 3.
Figure 7:
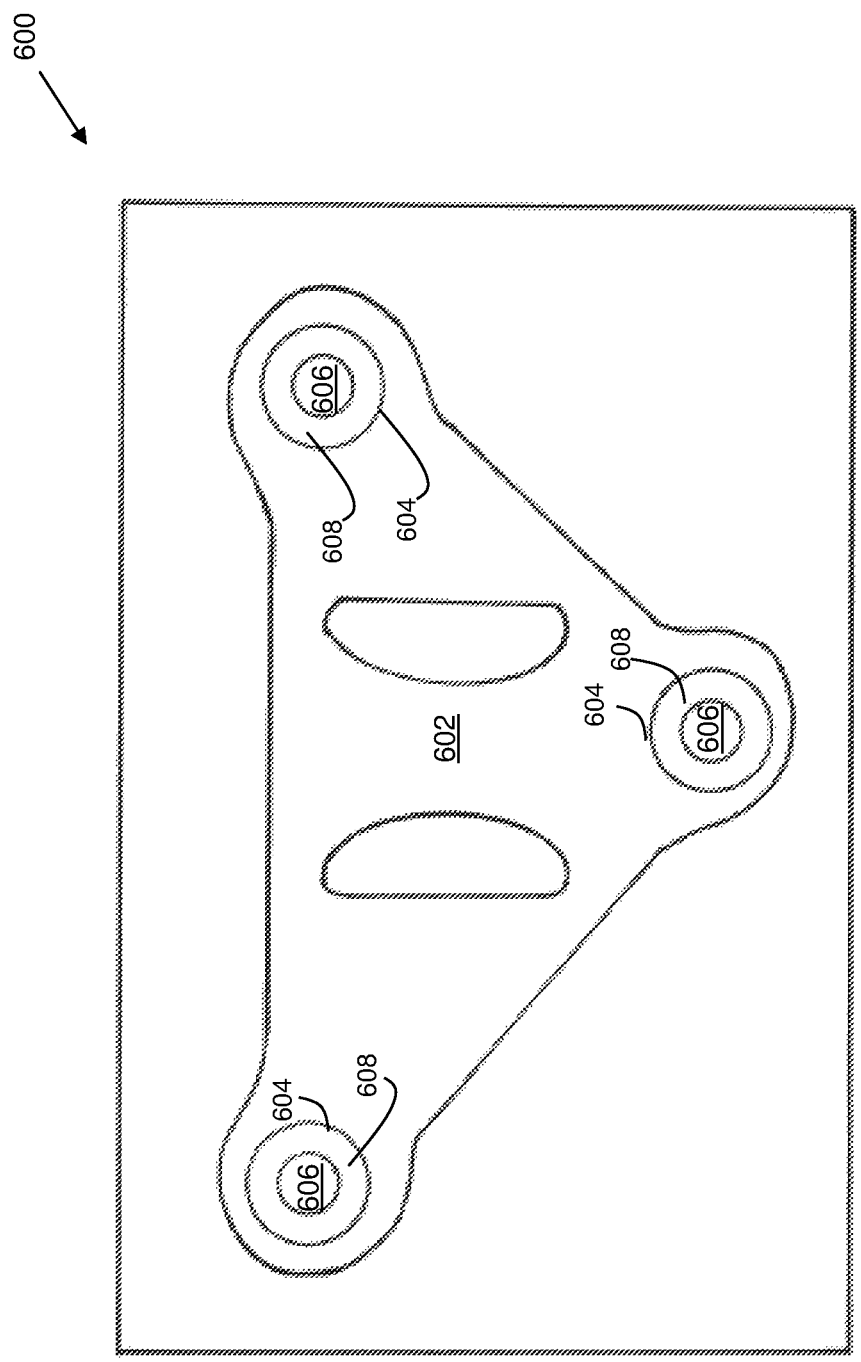
FIG. 7 is a diagram illustrating another example of the wearable apparatus, as shown in FIG. 6.
Figure 8:
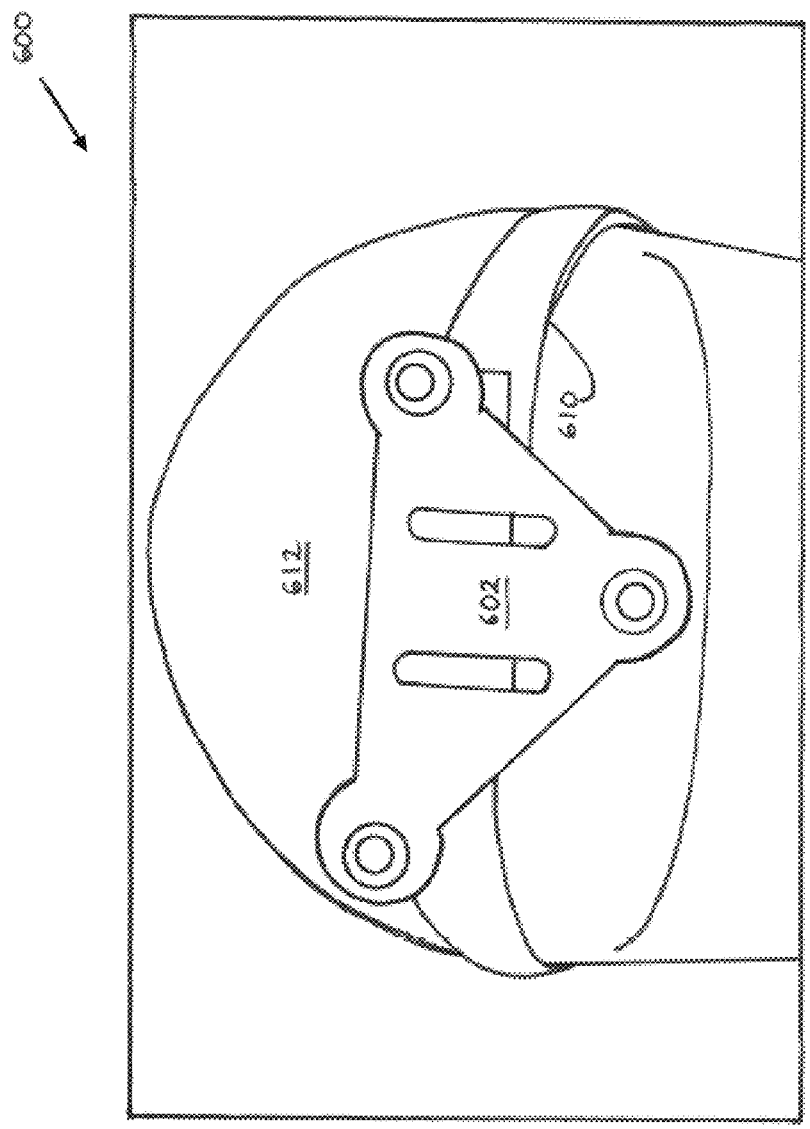
FIG. 8 is a diagram illustrating another example of the wearable apparatus, as shown in FIG. 6, and attachable to a head of a patient.

Referring now to FIGS. 6, 7, and 8, together, and referring back to FIG. 2, there diagrams illustrate a wearable apparatus 600, in accordance with embodiments of the present disclosure. Referring to FIG. 6, this diagram illustrates a wearable apparatus 600 usable with the medical navigation system 205 and the control and processing system 300, as respectively shown in FIGS. 2 and 3, in accordance with an embodiment of the present disclosure. Referring to FIG. 7, this diagram illustrates another example of the wearable apparatus 600, as shown in FIG. 6, in accordance with an embodiment of the present disclosure. Referring to FIG. 8, this diagram illustrates another example of the wearable apparatus 600, as shown in FIG. 6, and attachable to a head of a patient 202, as shown in FIG. 2, in accordance with an embodiment of the present disclosure. FIGS. 6-8 are described, together, with like elements being referred to with like reference numerals.

Still referring now to FIGS. 2, 6, 7, and 8, together, the apparatus 600 may be visible by both a three dimensional (3D) scanner system, e.g., 3D scanner 309, of a medical navigation system 205, such as the medical navigation system 205, and a camera of the medical navigation system 205, such as the camera 307. In one example, the apparatus 600 may be wearable. The wearable apparatus includes a rigid member 602 and a plurality of markers 604 attached to the rigid member 602. Each of the plurality of markers 604 includes a reflective surface portion 606 visible by the camera 307 and a distinct identifiable portion 608 visible by the 3D scanner 309. In one example, the distinct identifiable portion 608 comprises a distinct colour portion. The wearable apparatus 600 further has a connector mechanism (not shown) to connect the apparatus 600 to a reference location. The apparatus 600 may be located in a field of view of the 3D scanner system and the camera within a timeframe of the 3D scan.

Still referring now to FIGS. 2, 6, 7, and 8, together, in one example, the timeframe may be at least one frame of the 3D scan. The reference location may be a fixed location, such as on a Mayfield clamp, a bed, or a stretcher. Alternatively, the reference location includes being attached onto a patient, either simply resting on the patient for a short time during at least one frame of the 3D scan, or fixed to the patient, for example using medical grade tape, an adhesive, Velcro, or any other suitable fastener. The apparatus may be sterilizable. The field of view may also include a patient reference.

Still referring now to FIGS. 2, 6, 7, and 8, together, in one example, the wearable apparatus 600 may have at least three markers 604. However, any number of markers 604 may be used to meet the criteria of a particular implementation. The rigid member 602 may be a rigid surface member with at least three markers 604 mounted thereon. In one example, the rigid member 602 may be planar and substantially rigid in shape. The reflective surface portions 606 may include an identifiable surface, which in one example may be a retroreflective surface. The rigid member 602 is shown in an approximate shape of a triangle; however, any suitable shape may be used to meet the criteria of a particular implementation.

Still referring now to FIGS. 2, 6, 7, and 8, together, in one example, the apparatus 600 may take the form of a flexible, e.g., non-rigid, cap or bandage that may be either placed on, stuck to, or affixed to the patient 202. In one example, the markers 604 on the bandage could be placed in a geometric position to represent a valid tracking tool having reflective markers. In one example, such a bandage may be recognizable by tracking system 321 of the medical navigation system 205, e.g., defined in ROM file saved in data storage device 342, and recognized as a valid trackable tool by the tracking system 321.

Still referring now to FIGS. 6, 7, and 8, together, in one example, at least three markers 604 may be all mounted on the rigid member 602 at unique distances from each other with the distinct identifiable portion 608 of each of the markers 604 being a distinct colour from the others of the markers 604. In another example, at least three markers 604 are all mounted on the rigid member 602 at unique distances from each other with the distinct identifiable portion 608 of each of the three markers 604 being the same colour but distinct in colour from the rigid member 602.

Still referring now to FIGS. 2, 6, 7, and 8, together, in one example, each of the plurality of markers 604 comprises a first identifiable shape and a second larger identifiable shape disposed around the first identifiable shape, wherein the first identifiable shape comprises the reflective surface portion 606 and the second identifiable shape comprises the distinct identifiable portion 608. In one example, the first identifiable shape may be a circle and the second identifiable shape may be a circular ring. While circular shapes and circular rings are provided as example shapes for the reflective surface portion 606 and the distinct identifiable portion 604, any suitable shapes may be used to meet the criteria of a particular implementation. The circular configuration of the markers 604 allows for orientation-independent adhesion while the unique spacing between markers 604 allows for real time tracking of the overall tool 600 orientation.

Still referring now to FIGS. 2, 6, 7, and 8, together, in one example, the wearable apparatus 600 further has a strap 610 (FIG. 8) connected to the rigid member 602 for securing the wearable apparatus 600 to the patient 202. In one example, the strap 610 is attachable around a head 612 of the patient. In another example, the wearable apparatus 600 is securable to the patient 202 using a medical adhesive. While the strap 610 and a medical adhesive have been provided as examples, any suitable fastener may be used to attach the apparatus 600 to the patient 202. The apparatus 600 may be configured such that the apparatus or tool 600 may be attached in a variety of ways based on the adhesive used. Some examples for placement are attaching the apparatus 600 to a headband or directly to the shaved head 612 surface using medical adhesive. In another example, as described above, the apparatus 600 comprises a flexible bandage having an adhesive on the back side for affixing to the patient 202.

Still referring now to FIGS. 2, 6, 7, and 8, together, and referring back to FIG. 3, following the target extraction in both the tracking system 321 space and 3D scanner 309 space, a transformation mapping can be modeled to relate the tracking system 321 space with the 3D scanner 309 space. Once the 3D scanner 309 point cloud is mapped to the MR/CT coordinates by applying a surface matching method between an extracted surface of the MR/CT to the point cloud, the apparatus 600 transformation allows registration between the tracking system 321 and the MR/CT image data.

Still referring now to FIGS. 2, 6, 7, and 8, together, conventional approaches use a reference star that has five positioning targets that are retro-reflective with no additional colour that can be seen by the 3D scanner and the infrared optical tracking system. In contrast, the apparatus 600 has, in one example, only three markers 604 and uses substantially flat targets. The conventional reference star also uses larger distances between positioning targets and is placed beside the patient 202, rather than on the patient 202. Retro-reflective markers are also used by some 3D scanners as passive markers to assist with stitching individual frames within a point cloud and improve overall accuracy of 3D scans. Two examples of companies that sell target stickers as part of their 3D scanner portfolio are Creaform® and LabelID™.

Figure 9:
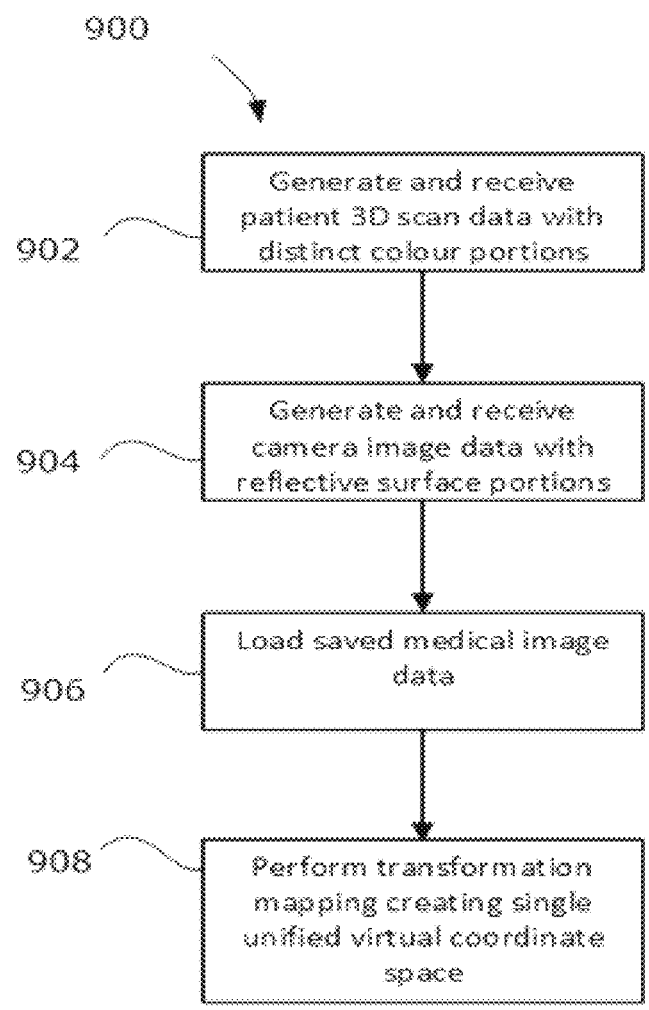
FIG. 9 is a flow chart illustrating a method of registering a patient for a medical procedure via a medical navigation system and using a wearable apparatus.

Referring to FIG. 9, this flow chart illustrates a method 900 of registering a patient for a medical procedure via a medical navigation system 205 and using a wearable apparatus, such as the wearable apparatus 600, in accordance with an embodiment of the present disclosure. The method 900 is performed to register a patient 202 for a medical procedure with a medical navigation system, such as the medical navigation system 205 (FIG. 2), using a wearable apparatus, e.g., the apparatus 600, visible by both a three dimensional (3D) scanner system, e.g., including the 3D scanner 309 (FIG. 3), of the medical navigation system 205 and a camera, e.g., the camera 307 (FIG. 3), of the medical navigation system 205. The method may be controlled and/or executed, for example by the processor 302 (FIG. 3) of the control and processing unit 300 (FIG. 3) that forms part of the medical navigation system 205 (FIG. 2).

Still referring to FIG. 9 and referring back to FIGS. 2 and 3, at a first block 902, the method 900 generates and receives 3D scan data from the 3D scanner 309 that is representative of a 3D scan of at least a portion of the patient 202. The 3D scan includes distinct identifiable portions of the wearable apparatus 600 that are visible by the 3D scanner 309. In one example, the distinct identifiable portions may be the distinct colour portions 608.

Still referring to FIG. 9 and referring back to FIGS. 2 and 3, next, at a block 904, the method 900 generates and receives image data from the camera 307. The image data includes reflective surface portions of the wearable apparatus 600 visible by the camera 307. In one example, the reflective surface portions may be the reflective surface portions 606. Next, at a block 906, the method 900 loads saved medical image data. The saved medical data includes preoperative image data, such as the pre-op image data 354, saved during a previous scan of at least a portion of the patient 202. The pre-op image data 354 comprises data from computerized tomography (CT) images, magnetic resonance imaging (MRI) images, positron emission topography (PET) images, contrast-enhanced CT images, X-ray images, ultrasound images, or any other suitable medical imaging source. While the blocks 902, 904, and 906 are shown as being performed in a particular order, blocks 902, 904, and 906 may be performed in any suitable order, including concurrently performed.

Still referring to FIG. 9 and referring back to FIGS. 2, 3, and 5, next, at a block 908, the method 900 performs a transformation mapping to create a single unified virtual coordinate space based on the 3D scan data, the image data, and the medical image data. In one example, the transformation may be similar to or based on the registration process, as described in connection with FIG. 5. In another example, the transformation mapping includes a surface matching approach using a 3D scanner point cloud based on the 3D scan data and at least one of MR and CT coordinates. In another example, the camera 307 of the medical navigation system 205 may form part of a tracking system, such as the tracking system 321, and the transformation mapping may further include registering the tracking system 321 to create a single unified virtual coordinate space for the 3D scanner point cloud, at least one of the MR and CT coordinates, and the image data from the tracking system. However any suitable known or yet to be developed transformation process may be applied.

Still referring to FIG. 9 and referring back to FIGS. 2 and 3, in one slightly modified example of the method 900, the 3D scanner 309 is affixed to an end effector of a robot, such as the robotic arm 305. The robotic arm 305 may also have tracking markers affixed thereto that are visible by a camera, such as the camera 307, of the tracking system 321. The robotic arm 305 may perform the 3D scan, e.g., block 902. Since the position of the robotic arm 305, and, consequently, the 3D scanner position, are known to the tracking system 321, e.g., as a result of block 904, and since the distance from the 3D scanner to the patient 202 being scanned can be calculated by the processing unit 300 using the data from the 3D scanner, a starting point cloud can be generated at a known position relative to the tracking markers affixed to the robotic arm 305. Subsequently, the 3D scanner 309 can be moved free-hand by a doctor or technician without the need to be tracked by the tracking system 321, which allows the 3D scanner 309 to be moved out of a line of sight of the camera 307 of the tracking system 321. The subsequent point clouds are stitched onto the starting point cloud, thereby resulting in a complete surface in a known location relative to the tracking system 321. This surface can then be registered to the surface of MRI data, e.g., the block 908 performing the transformation mapping, thereby resulting in a complete transformation from the MRI data to the tracking system 321. In another example, two separate 3D scanners 309 may be used, one 3D scanner 309 that remains fixed to the robotic arm 305 and one 3D scanner 309 that may be used free hand by a doctor or technician. In this approach, the 3D scanner 309 on the end effector of the robotic arm 305 is disposed at a fixed point and is used to generate the cloud point to tracking system 321 coordinates. Subsequently, data from the free-hand 3D scanner 309 can be used to register new frames to original frames from the fixed 3D scanner data using continuously stitching.

Still referring to FIG. 9 and referring back to FIGS. 3 and 6, in one example of the method 900, the wearable apparatus 600 comprises a plurality of markers 604 attached to a rigid member 602 (of the wearable apparatus 600), wherein each of the plurality of markers 604 comprises one of the reflective surface portions 606 visible by the camera 307 and one of the distinct identifiable portions 608 visible by the 3D scanner 309. In one example, the wearable apparatus 600 has at least three markers 604 and the rigid member 602 is a substantially rigid surface with the at least three markers 604 thereon mounted.

Still referring to FIG. 9 and referring back to FIG. 6, in one example of the method 900, at least three markers 604 may be all mounted on the rigid member 602 at unique distances from each other with the distinct identifiable portion 608 of each of the markers 604 being a distinct colour from the others of the markers 604. In another example, at least three markers 604 may be all mounted on the rigid member 602 at unique distances from each other with the distinct identifiable portion 608 of each of the three markers 604 being the same colour but distinct in colour from the rigid member 602.

Still referring to FIG. 9 and referring back to FIG. 6, in one example of the method 900, each of the plurality of markers 604 comprises a first identifiable shape and a second larger identifiable shape around the first identifiable shape where the first identifiable shape includes the reflective surface portion 606 and the second larger identifiable shape includes the distinct identifiable portion 608. In one example, the first identifiable shape may be a circle and the second larger identifiable shape may be a circular ring. While circular shapes and circular rings are provided as example shapes for the reflective surface portion 606 and the distinct identifiable portion 608, any suitable shapes may be used to meet the criteria of a particular implementation. The circular configuration of the markers 604 allow for orientation-independent adhesion while the unique spacing between markers 604 allows for real time tracking of the overall tool 600 orientation.

Still referring to FIG. 9 and referring back to FIGS. 2, 6, and 8, in one example of the method 900, the wearable apparatus 600 further comprises a strap 610 (FIG. 8) connected to the rigid member 602 for securing the wearable apparatus 600 to a patient. In one example, the strap 610 is attachable around a head 612 of the patient. In another example, the wearable apparatus 600 is securable to a patient using a medical adhesive. While the strap 610 and a medical adhesive have been provided as examples, any suitable fastening means may be used to attach the apparatus 600 to the patient 202. The apparatus 600 is configured such that the apparatus or tool 600 may be attached in a variety of ways based on the adhesive used. Some examples for placement are attaching the apparatus 600 to a headband or directly to the shaved head 612 surface using medical adhesive.

Still referring to FIG. 9 and referring back to FIGS. 2, 3, 6, and 8, in one example, the apparatus 600 comprises a flexible, e.g., non-rigid, cap or bandage that may be either placed on, stuck to, or affixed to the patient 202. In one example, the markers 604 on the bandage could be placed in a geometric position to represent a valid tracking tool having reflective markers. In one example, such a bandage is recognizable by tracking system 321 of the medical navigation system 205, e.g., defined in a ROM file saved in the data storage device 342, and recognized as a valid trackable tool by the tracking system 321.

Figure 10:
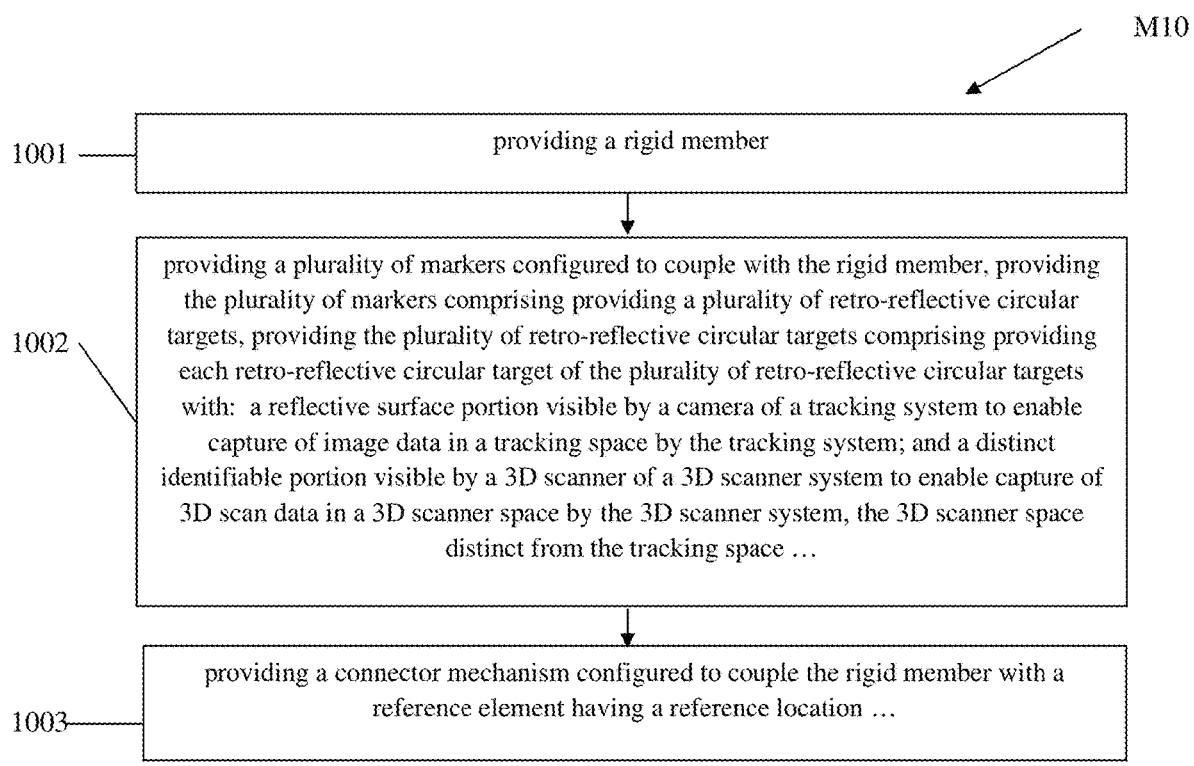
FIG. 10 is a flow chart illustrating a method of providing an apparatus for registration in a medical procedure.

Referring to FIG. 10, this flow chart illustrates a method M10 of providing an apparatus 600 for registration in a medical procedure, in accordance with an embodiment of the present disclosure. The method M10 comprises: providing a rigid member 602, as indicated by block 1001; providing a plurality of markers 604 configured to couple with the rigid member 602, providing the plurality of markers 604 comprising providing a plurality of retro-reflective circular targets, providing the plurality of retro-reflective circular targets comprising providing each retro-reflective circular target of the plurality of retro-reflective circular targets with: a reflective surface portion 606 visible by a camera 307 of a tracking system 321 to enable capture of image data in a tracking space by the tracking system 321; and a distinct identifiable portion 608 visible by a 3D scanner 309 of a 3D scanner system to enable capture of 3D scan data in a 3D scanner space by the 3D scanner system, the 3D scanner space distinct from the tracking space, as indicated by block 1002; and providing a connector mechanism (not shown) configured to couple the rigid member 602 with a reference element having a reference location, as indicated by block 1003, providing each retro-reflective circular target comprising providing each reflective surface portion with an infrared (IR) retro-reflective center for visibility by the camera 307 of the tracking system, providing each retro-reflective circular target comprising providing each distinct identifiable portion 608 with a contrasting coloured ring for enabling image data extraction from a colour point cloud collected by the colour 3D scanner system, providing each distinct identifiable portion 608 with a contrasting coloured ring comprising providing each contrasting coloured ring with a contrasting colour distinct from another contrasting coloured ring, and providing the plurality of retro-reflective circular targets comprising providing the plurality of retro-reflective circular targets configured to facilitate stitching individual frames within the colour point cloud and improving accuracy of a 3D scan by the 3D scanner of the 3D scanner 309 system.

Still referring to FIG. 10, in the method M10, providing the plurality of markers 604, as indicated by block 1002, comprises one of: providing the plurality of markers 604 comprising providing at least three markers 604; providing each marker 604 of the plurality of markers 604 comprising configuring each marker 604 to couple with the rigid member 602 at a unique distance in relation to another marker 604 of the plurality of markers 604; providing each marker 604 of the plurality of markers comprising providing the distinct identifiable portion 608 of each marker 604 of the plurality of markers 604 with a distinct colour in relation to another marker 604 of the plurality of markers 604; providing each marker 604 of the plurality of markers 604 comprising providing the distinct identifiable portion 608 of each marker 604 of the plurality of markers 604 with a distinct colour in relation to a colour of the rigid member 602; and providing each marker 604 of the plurality of markers 604 comprising providing each marker 604 with a first identifiable shape and a second identifiable shape disposed around the first identifiable shape.

Still referring to FIG. 10, in the method M10, providing the rigid member 602 as indicated by block 1001, comprises at least one of: providing the rigid member 602 as substantially rigid; providing the rigid member 602 comprising a planar shape; providing the rigid member 602 as configured to couple with a patient 202 using a medical adhesive; and providing the rigid member 602 as configured to couple with a flexible member, the flexible member configured to couple with a patient 202. Providing the rigid member 602 comprises configuring the rigid member 602 to couple with a flexible member comprises providing at least one of a bandage and a sticker Still referring to FIG. 10, in the method M10, providing the plurality of markers 604, as indicated by block 1002, comprises at least one of: providing the first identifiable shape comprising the reflective surface portion 606; providing the second identifiable shape comprising the distinct identifiable portion 608, and providing the reflective surface portion 606 comprising a surface identifiable by the camera 307.

Still referring to FIG. 10, the method M10 further comprises providing a strap configured to couple the rigid member 602 with a patient 202. Providing the strap comprises providing the strap as attachable around a head of the patient 202. Providing the connector mechanism, as indicated by block 1003, comprises providing the connector mechanism configured to couple the rigid member 602 with the reference element having the reference location comprising a fixed location in relation to at least one of a Mayfield clamp, a bed, a stretcher; and a portion of a patient 202. In the method M10, the apparatus 600 is at least one of wearable and sterilizable.

Figure 11:
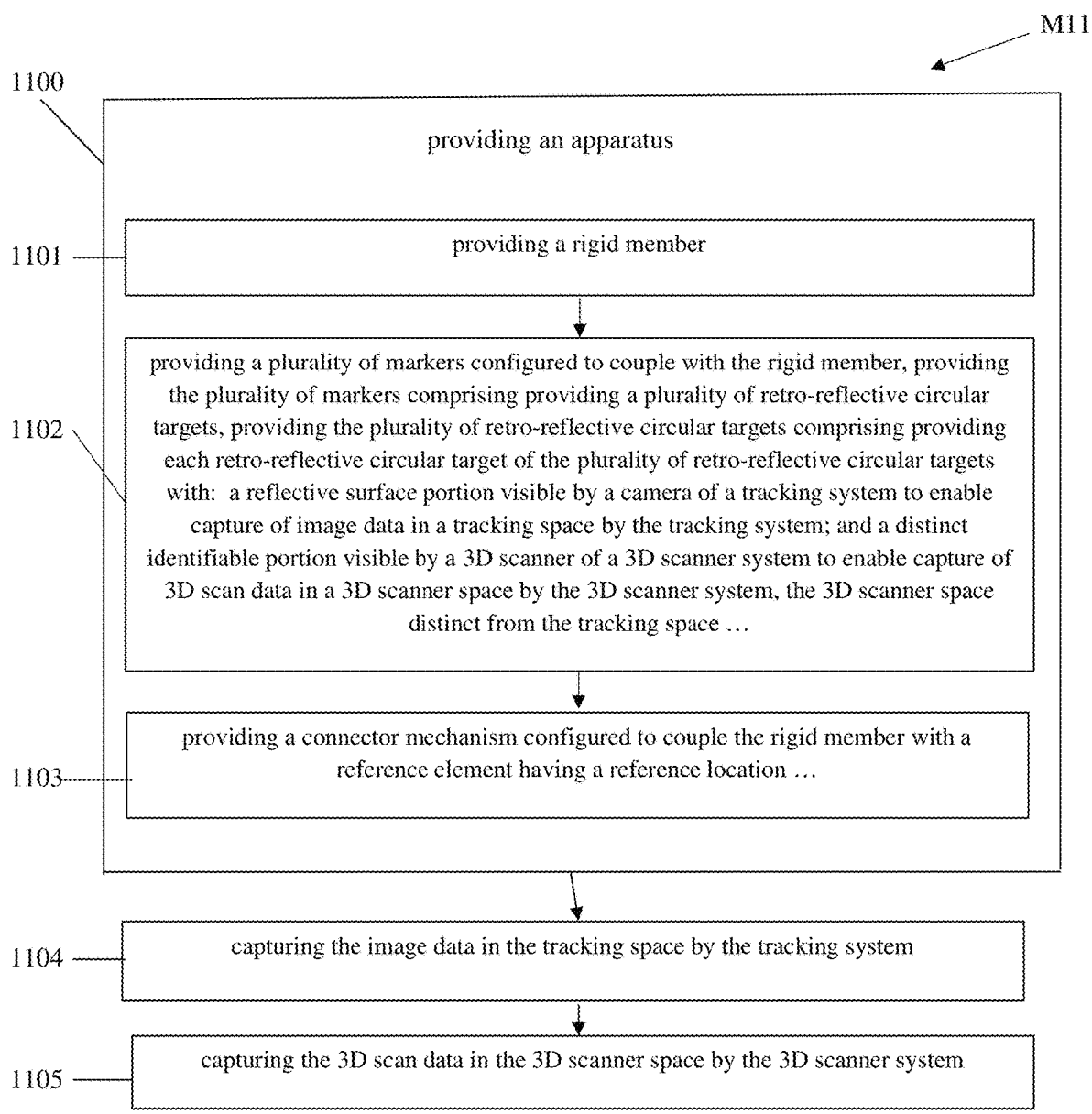
FIG. 11 is a flow chart illustrating a method for registration in a medical procedure by way of an apparatus.

Referring to FIG. 11, this flow chart illustrates a method M11 for registration in a medical procedure by way of an apparatus 600, in accordance with an embodiment of the present disclosure. The method for M11 comprises: providing the apparatus 600, as indicated by block 1100, providing the apparatus 600 comprising: providing a rigid member 602, as indicated by block 1101; providing a plurality of markers 604 configured to couple with the rigid member 602, providing the plurality of markers 604 comprising providing a plurality of retro-reflective circular targets, providing the plurality of retro-reflective circular targets comprising providing each retro-reflective circular target of the plurality of retro-reflective circular targets with: a reflective surface portion 606 visible by a camera 307 of a tracking system 321 to enable capture of image data in a tracking space by the tracking system 321; and a distinct identifiable portion 608 visible by a 3D scanner 309 of a 3D scanner system to enable capture of 3D scan data in a 3D scanner space by the 3D scanner system, the 3D scanner space distinct from the tracking space, as indicated by block 1102; and providing a connector mechanism (not shown) configured to couple the rigid member 602 with a reference element having a reference location, as indicated by block 1103, providing each retro-reflective circular target comprising providing each reflective surface portion 606 with an infrared (IR) retro-reflective center for visibility by the camera of the tracking system, providing each retro-reflective circular target comprising providing each distinct identifiable portion 608 with a contrasting coloured ring for enabling image data extraction from a colour point cloud collected by the colour 3D scanner system, providing each distinct identifiable portion 608 with a contrasting coloured ring comprising providing each contrasting coloured ring with a contrasting colour distinct from another contrasting coloured ring, and providing the plurality of retro-reflective circular targets comprising providing the plurality of retro-reflective circular targets configured to facilitate stitching individual frames within the colour point cloud and improving accuracy of a 3D scan by the 3D scanner 309 of the 3D scanner system 321; and capturing the image data in the tracking space by the tracking system, as indicated by block 1104; and capturing the 3D scan data in the 3D scanner space by the 3D scanner system, as indicated by block 1105.

Still referring to FIG. 11, in the method M11, providing the plurality of markers 604, as indicated by block 1102, comprises one of: providing the plurality of markers 604 comprising providing at least three markers 604; providing each marker 604 of the plurality of markers 604 comprising configuring each marker 604 to couple with the rigid member 602 at a unique distance in relation to another marker 604 of the plurality of markers 604; providing each marker 604 of the plurality of markers 604 comprising providing the distinct identifiable portion 608 of each marker 604 of the plurality of markers 604 with a distinct colour in relation to another marker 604 of the plurality of markers 604; providing each marker 604 of the plurality of markers 604 comprising providing the distinct identifiable portion 608 of each marker 604 of the plurality of markers 604 with a distinct colour in relation to a colour of the rigid member 602; and providing each marker 604 of the plurality of markers 604 comprising providing each marker 604 with a first identifiable shape and a second identifiable shape disposed around the first identifiable shape.

The above described specific embodiments have been shown by way of example and understood is that these embodiments may be susceptible to various modifications and alternative forms. Further understood is that the claims are not intended to be limited to the particular forms disclosed, but rather to cover modifications, equivalents, and alternatives falling within the spirit and scope of the present disclosure.

What is claimed:

1. An apparatus for registration in a medical procedure, the apparatus comprising:
   a rigid member;
   a plurality of markers configured to couple with the rigid member, the plurality of markers comprising a plurality of retro-reflective circular targets, each retro-reflective circular target of the plurality of retro-reflective circular targets comprising:
   a reflective surface portion visible by a camera of a tracking system to enable capture of image data in a tracking space by the tracking system; and
   a distinct identifiable portion visible by a 3D scanner of a colour 3D scanner system to enable capture of 3D scan data in a 3D scanner space by the colour 3D scanner system, the 3D scanner space distinct from the tracking space; and
   a connector mechanism configured to couple the rigid member with a reference element having a reference location;
   wherein the reflective surface portion further comprises an infrared (IR) retro-reflective center for visibility by the camera of the tracking system;
   wherein the distinct identifiable portion further comprises a contrasting coloured ring for enabling image data extraction from a colour point cloud collected by the colour 3D scanner system;
   wherein the contrasting coloured ring further comprises a contrasting colour distinct from another contrasting coloured ring;
   wherein the plurality of retro-reflective circular targets facilitates stitching individual frames within the colour point cloud and improving accuracy of a 3D scan by the 3D scanner of the colour 3D scanner system;
   wherein the plurality of retro-reflective circular targets facilitates continuously stitching of subsequent colour point clouds onto a starting colour point cloud, thereby determining a complete surface in a known location relative to the tracking system;

wherein the plurality of retro-reflective circular targets facilitates registering the complete surface to a surface from MRI data, thereby determining a complete transformation from the MRI data relative to the tracking system; and wherein the plurality of retro-reflective circular targets facilitates updating navigation information stored in the memory to include a single unified virtual coordinate space and to register the 3D scanner space, the MRI data, and the image data in the single unified virtual coordinate space.

2. The apparatus of claim 1, wherein one of: the plurality of markers comprises at least three markers; each marker of the plurality of markers is configured to couple with the rigid member at a unique distance in relation to another marker of the plurality of markers; the distinct identifiable portion of each marker of the plurality of markers comprises a distinct colour in relation to another marker of the plurality of markers; the distinct identifiable portion of each marker of the plurality of markers comprises a distinct colour in relation to a colour of the rigid member; and each marker of the plurality of markers comprises a first identifiable shape and a second identifiable shape disposed around the first identifiable shape.

3. The apparatus of claim 2, wherein at least one of: the reflective surface portion comprises the first identifiable shape; the distinct identifiable portion comprises the second identifiable shape; and the reflective surface portion comprises a surface identifiable by the camera.

4. The apparatus of claim 1, wherein at least one of: the rigid member comprises a planar shape; the rigid member is configured to couple with a patient using a medical adhesive; and the rigid member is configured to couple with a flexible member, the flexible member configured to couple with the patient.

5. The apparatus of claim 4, wherein the flexible member comprises at least one of a bandage and a sticker.

6. The apparatus of claim 1, further comprising a strap configured to couple the rigid member with a patient.

7. The apparatus of claim 6, wherein the strap is attachable around a head of the patient.

8. The apparatus of claim 1, wherein the reference location comprises a fixed location in relation to at least one of a Mayfield® clamp, a bed, a stretcher; and a portion of a patient.

9. The apparatus of claim 1, wherein the apparatus is at least one of wearable and sterilizable.

10. A method of providing an apparatus for registration in a medical procedure, the method comprising:

providing a rigid member;

providing a plurality of markers configured to couple with the rigid member, providing the plurality of markers comprising providing a plurality of retro-reflective circular targets, providing the plurality of retro-reflective circular targets comprising providing each retro-reflective circular target of the plurality of retro-reflective circular targets with:

a reflective surface portion visible by a camera of a tracking system to enable capture of image data in a tracking space by the tracking system; and a distinct identifiable portion visible by a 3D scanner of a colour 3D scanner system to enable capture of 3D scan data in a 3D scanner space by the colour 3D scanner system, the 3D scanner space distinct from the tracking space; and providing a connector mechanism configured to couple the rigid member with a reference element having a reference location, wherein the retro-reflective circular target further comprises an infrared (IR) retro-reflective center for visibility by the camera of the tracking system, wherein the retro-reflective circular target comprises the distinct identifiable portion with the contrasting coloured ring for enabling image data extraction from a colour point cloud collected by the colour 3D scanner system, wherein the plurality of retro-reflective circular targets further comprises retro-reflective circular targets configured to facilitate stitching individual frames within the colour point cloud and improving accuracy of a 3D scan by the 3D scanner of the colour 3D scanner system;

wherein the plurality of retro-reflective circular targets facilitates continuously stitching of subsequent colour point clouds onto a starting colour point cloud, thereby determining a complete surface in a known location relative to the tracking system;

wherein the plurality of retro-reflective circular targets facilitates registering the complete surface to a surface from MRI data, thereby determining a complete transformation from the MRI data relative to the tracking system; and wherein the plurality of retro-reflective circular targets facilitates updating navigation information stored in the memory to include a single unified virtual coordinate space and to register the 3D scanner space, the MRI data, and the image data in the single unified virtual coordinate space.

11. The method of claim 10, wherein providing the plurality of markers comprises one of: providing the plurality of markers comprising providing at least three markers; providing each marker of the plurality of markers comprising configuring each marker to couple with the rigid member at a unique distance in relation to another marker of the plurality of markers; providing each marker of the plurality of markers comprising providing the distinct identifiable portion of each marker of the plurality of markers with a distinct colour in relation to another marker of the plurality of markers; providing each marker of the plurality of markers comprising providing the distinct identifiable portion of each marker of the plurality of markers with a distinct colour in relation to a colour of the rigid member; and providing each marker of the plurality of markers comprising providing each marker with a first identifiable shape and a second identifiable shape disposed around the first identifiable shape.

12. The method of claim 11, wherein providing the plurality of markers comprises at least one of: providing the first identifiable shape comprising the reflective surface portion; providing the second identifiable shape comprising the distinct identifiable portion; and providing the reflective surface portion comprising a surface identifiable by the camera.

13. The method of claim 10, wherein providing the rigid member comprises at least one of: providing the rigid member comprising a planar shape; providing the rigid member as configured to couple with a patient using a medical adhesive; and providing the rigid member as configured to couple with a flexible member, the flexible member configured to couple with a patient.

14. The method of claim 13, wherein providing the rigid member as configured to couple with the flexible member comprises providing at least one of a bandage and a sticker.

15. The method of claim 10, further comprising providing a strap configured to couple the rigid member with a patient.

16. The method of claim 15, wherein providing the strap comprises providing the strap as attachable around a head of the patient.

17. The method of claim 10, wherein providing the connector mechanism comprises providing the connector mechanism configured to couple the rigid member with the reference element having the reference location comprising a fixed location in relation to at least one of a Mayfield clamp, a bed, a stretcher; and a portion of a patient.

18. The method of claim 10, wherein the apparatus is at least one of wearable and sterilizable.

19. A method for registration in a medical procedure by way of an apparatus, the method comprising:
providing the apparatus, providing the apparatus comprising:
 providing a rigid member;
 providing a plurality of markers configured to couple with the rigid member, providing the plurality of markers comprising providing a plurality of retro-reflective circular targets, providing the plurality of retro-reflective circular targets comprising providing each retro-reflective circular target of the plurality of retro-reflective circular targets with:
  a reflective surface portion visible by a camera of a tracking system to enable capture of image data in a tracking space by the tracking system; and
  a distinct identifiable portion visible by a 3D scanner of a colour 3D scanner system to enable capture of 3D scan data in a 3D scanner space by the colour 3D scanner system, the 3D scanner space distinct from the tracking space; and
 providing a connector mechanism configured to couple the rigid member with a reference element having a reference location,
 providing the each retro-reflective circular target comprising providing each reflective surface portion with an infrared (IR) retro-reflective center for visibility by the camera of the tracking system,
 providing the each retro-reflective circular target comprising providing each distinct identifiable portion with a contrasting coloured ring for enabling image data extraction from a colour point cloud collected by the colour 3D scanner system,
 providing the each distinct identifiable portion with a contrasting coloured ring comprising providing the each contrasting coloured ring with a contrasting colour distinct from another contrasting coloured ring, and
 providing the plurality of retro-reflective circular targets comprising providing the plurality of retro-reflective circular targets configured to facilitate stitching individual frames within the colour point cloud and improving accuracy of a 3D scan by the 3D scanner of the colour 3D scanner system; and
 capturing the image data in the tracking space by the tracking system; and
 capturing the 3D scan data in the 3D scanner space by the colour 3D scanner system;
wherein the plurality of retro-reflective circular targets facilitates continuously stitching of subsequent colour point clouds onto a starting colour point cloud, thereby determining a complete surface in a known location relative to the tracking system;
wherein the plurality of retro-reflective circular targets facilitates registering the complete surface to a surface from MRI data, thereby determining a complete transformation from the MRI data relative to the tracking system; and
wherein the plurality of retro-reflective circular targets facilitates updating navigation information stored in the memory to include a single unified virtual coordinate space and to register the 3D scanner space, the MRI data, and the image data in the single unified virtual coordinate space.

20. The method of claim 19, wherein providing the plurality of markers comprises one of: providing the plurality of markers comprising providing at least three markers; providing each marker of the plurality of markers comprising configuring each marker to couple with the rigid member at a unique distance in relation to another marker of the plurality of markers; providing each marker of the plurality of markers comprising providing the distinct identifiable portion of each marker of the plurality of markers with a distinct colour in relation to another marker of the plurality of markers; providing each marker of the plurality of markers comprising providing the distinct identifiable portion of each marker of the plurality of markers with a distinct colour in relation to a colour of the rigid member; and providing each marker of the plurality of markers comprising providing each marker with a first identifiable shape and a second identifiable shape disposed around the first identifiable shape.

* * * * *